US012380557B2

(12) United States Patent
Hirokawa et al.

(10) Patent No.: US 12,380,557 B2
(45) Date of Patent: Aug. 5, 2025

(54) IMAGE PROCESSING METHOD, IMAGE PROCESSING DEVICE, AND PROGRAM

(71) Applicant: NIKON CORPORATION, Tokyo (JP)

(72) Inventors: Mariko Hirokawa, Yokohama (JP); Yasushi Tanabe, Fujisawa (JP)

(73) Assignee: NIKON CORPORATION, Tokyo (JP)

( * ) Notice: Subject to any disclaimer, the term of this patent is extended or adjusted under 35 U.S.C. 154(b) by 490 days.

(21) Appl. No.: 17/769,299

(22) PCT Filed: Oct. 15, 2019

(86) PCT No.: PCT/JP2019/040484
§ 371 (c)(1),
(2) Date: Apr. 14, 2022

(87) PCT Pub. No.: WO2021/074963
PCT Pub. Date: Apr. 22, 2021

(65) Prior Publication Data
US 2023/0130244 A1    Apr. 27, 2023

(51) Int. Cl.
*G06T 7/00* (2017.01)
*A61B 3/12* (2006.01)
(Continued)

(52) U.S. Cl.
CPC .............. *G06T 7/0012* (2013.01); *A61B 3/12* (2013.01); *A61B 5/02007* (2013.01); *G06T 7/11* (2017.01);
(Continued)

(58) Field of Classification Search
CPC ......... G06T 7/0012; G06T 7/11; G06T 7/155; G06T 7/194; G06T 11/001;
(Continued)

(56) References Cited

U.S. PATENT DOCUMENTS 10,628,940 B2 * 4/2020 Srivastava ............ G06T 7/0016
2013/0093870 A1 * 4/2013 Shibutani ............. A61B 3/1225
348/78
(Continued)

FOREIGN PATENT DOCUMENTS

JP       2016-093538 A    5/2016
WO   WO-2017/150583 A1    9/2017
(Continued)

OTHER PUBLICATIONS

Kim, "Wide-field Imaging of Retinal Diseases" 2015 US Ophthalmic Review, 2015;8(2):125-131. (Year: 2015).*
(Continued)

*Primary Examiner* — Juan A Torres
(74) *Attorney, Agent, or Firm* — Foley & Lardner LLP

(57) ABSTRACT

A processor divides a fundus region of an ultra-wide field fundus image into plural areas including at least a first area and a second area, generates first attribute information indicating an attribute of the first area and second attribute information indicating an attribute of the second area, and generates first mode instruction information to instruct display of the first area in a first mode corresponding to the first attribute information, and generates second mode instruction information to instruct display of the second area in a second mode corresponding to the second attribute information.

13 Claims, 21 Drawing Sheets

(51) Int. Cl.
*A61B 5/02* (2006.01)
*G06T 7/11* (2017.01)
*G06T 7/155* (2017.01)
*G06T 7/194* (2017.01)
*G06T 11/00* (2006.01)

(52) U.S. Cl.
CPC .............. *G06T 7/155* (2017.01); *G06T 7/194* (2017.01); *G06T 11/001* (2013.01); *G06T 2207/20152* (2013.01); *G06T 2207/30041* (2013.01); *G06T 2207/30101* (2013.01)

(58) Field of Classification Search
CPC . G06T 2207/20152; G06T 2207/30041; G06T 2207/30101; G06T 11/00; A61B 3/12; A61B 5/02007; A61B 3/1005; A61B 3/1025; A61B 2576/02; A61B 5/742; A61B 5/004; A61B 3/0025; A61B 3/102
USPC ......................................................... 382/128
See application file for complete search history.

(56) References Cited

U.S. PATENT DOCUMENTS

| | | | |
|---|---|---|---|
| 2017/0100030 A1* | 4/2017 | Bedworth | A61B 3/0033 |
| 2017/0296049 A1* | 10/2017 | Uji | G06T 5/73 |
| 2017/0367889 A1* | 12/2017 | Swan | A61F 9/00821 |
| 2018/0360304 A1 | 12/2018 | Kano et al. | |
| 2019/0082956 A1* | 3/2019 | Li | G02B 26/105 |
| 2019/0159673 A1* | 5/2019 | Yates | A61B 3/14 |
| 2020/0320692 A1* | 10/2020 | Fleming | G16H 30/40 |
| 2020/0359888 A1 | 11/2020 | Hirokawa et al. | |
| 2020/0387007 A1 | 12/2020 | Mizuta | |

FOREIGN PATENT DOCUMENTS

| | | |
|---|---|---|
| WO | WO-2019/130583 A1 | 7/2019 |
| WO | WO-2019/163911 A1 | 8/2019 |

OTHER PUBLICATIONS

Manivannan, "Ultra-wide-field fluorescein angiography of the ocular fundus." American journal of ophthalmology 140.3 (2005): 525-527 (Year: 2005).*

JP Office Action issued in corresponding Japanese Patent Application No. 2021-552012, dated Sep. 13, 2022 (6 pages).

* cited by examiner

IMAGE PROCESSING METHOD, IMAGE PROCESSING DEVICE, AND PROGRAM The technology disclosed herein relates to an image processing method, an image processing device, and a program.

BACKGROUND ART

The specification of U.S. Pat. No. 8,636,364 discloses identifying positions of vortex veins from a fundus image.

There is a desire to be able to detect abnormal areas in a fundus image.

SUMMARY OF INVENTION

An image processing method of a first aspect of technology disclosed herein includes a processor dividing a fundus region of an ultra-wide field fundus image into plural areas including at least a first area and a second area, the processor generating first attribute information indicating an attribute of the first area and second attribute information indicating an attribute of the second area, and the processor generating first mode instruction information to instruct display of the first area in a first mode corresponding to the first attribute information and second mode instruction information to instruct display of the second area in a second mode corresponding to the second attribute information.

An image processing method of a second aspect of technology disclosed herein is an image processing method including a processor dividing a fundus region of an ultra-wide field fundus image into plural areas according to a watershed of a choroidal vascular network, and the processor generating plural mode instruction information to instruct display in a mode corresponding to each area of the plural areas.

An image processing device of a third aspect of technology disclosed herein includes a memory, and a processor coupled to the memory. The processor divides a fundus region of an ultra-wide field fundus image into a plurality of areas including at least a first area and a second area, generates first attribute information indicating an attribute of the first area, and second attribute information indicating an attribute of the second area, and generates first mode instruction information to instruct display of the first area in a first mode corresponding to the first attribute information, and generates second mode instruction information to instruct display of the second area in a second mode corresponding to the second attribute information.

A program of a fourth aspect of technology disclosed herein causes a computer to execute processing including dividing a fundus region of an ultra-wide field fundus image into plural areas including at least a first area and a second area, generating first attribute information indicating an attribute of the first area and second attribute information indicating an attribute of the second area, and generating first mode instruction information to instruct display of the first area in a first mode corresponding to the first attribute information and second mode instruction information to instruct display of the second area in a second mode corresponding to the second attribute information.

DESCRIPTION OF EMBODIMENTS

Detailed explanation follows regarding a first exemplary embodiment of the technology disclosed herein, with reference to the drawings.

Figure 1:
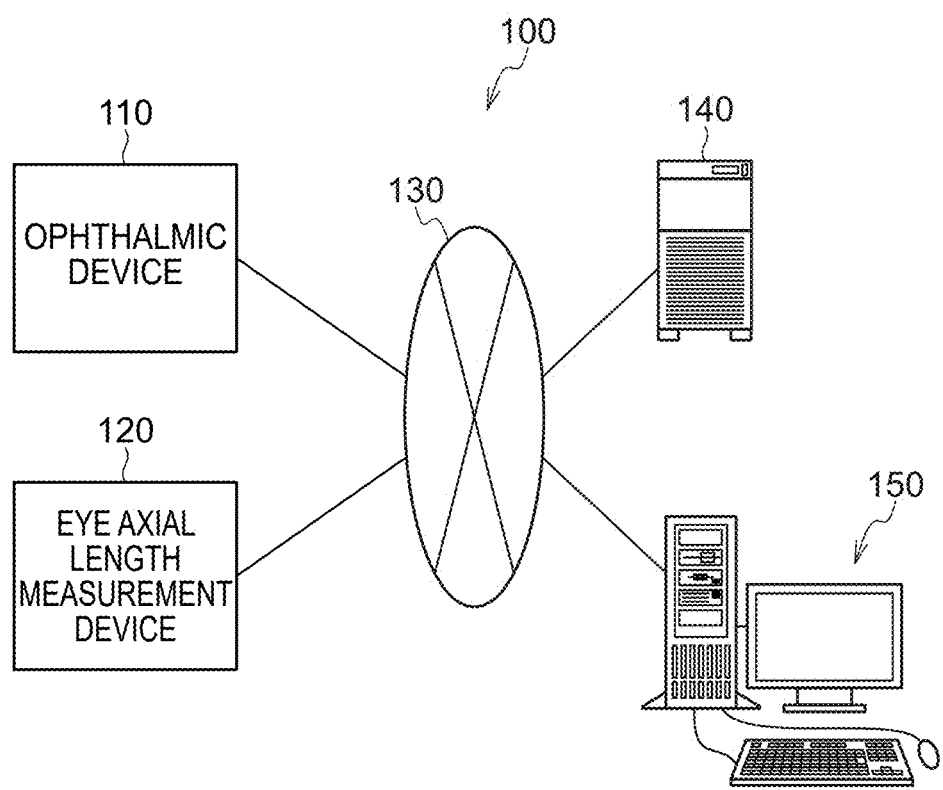
FIG. 1 is a block diagram of an ophthalmic system 100.

Explanation follows regarding a configuration of an ophthalmic system 100, with reference to FIG. 1. As illustrated in FIG. 1, the ophthalmic system 100 includes an ophthalmic device 110, an eye axial length measurement device 120, a management server device (referred to hereafter as "server") 140, and an image display device (referred to hereafter as "viewer") 150. The ophthalmic device 110 acquires an image of the fundus. The eye axial length measurement device 120 measures the axial length of the eye of a patient. The server 140 stores fundus images that were obtained by imaging the fundus of patients using the ophthalmic device 110 in association with patient IDs. The viewer 150 displays medical information such as fundus images acquired from the server 140.

The ophthalmic device 110, the eye axial length measurement device 120, the server 140, and the viewer 150 are connected together through a network 130.

Figure 2:
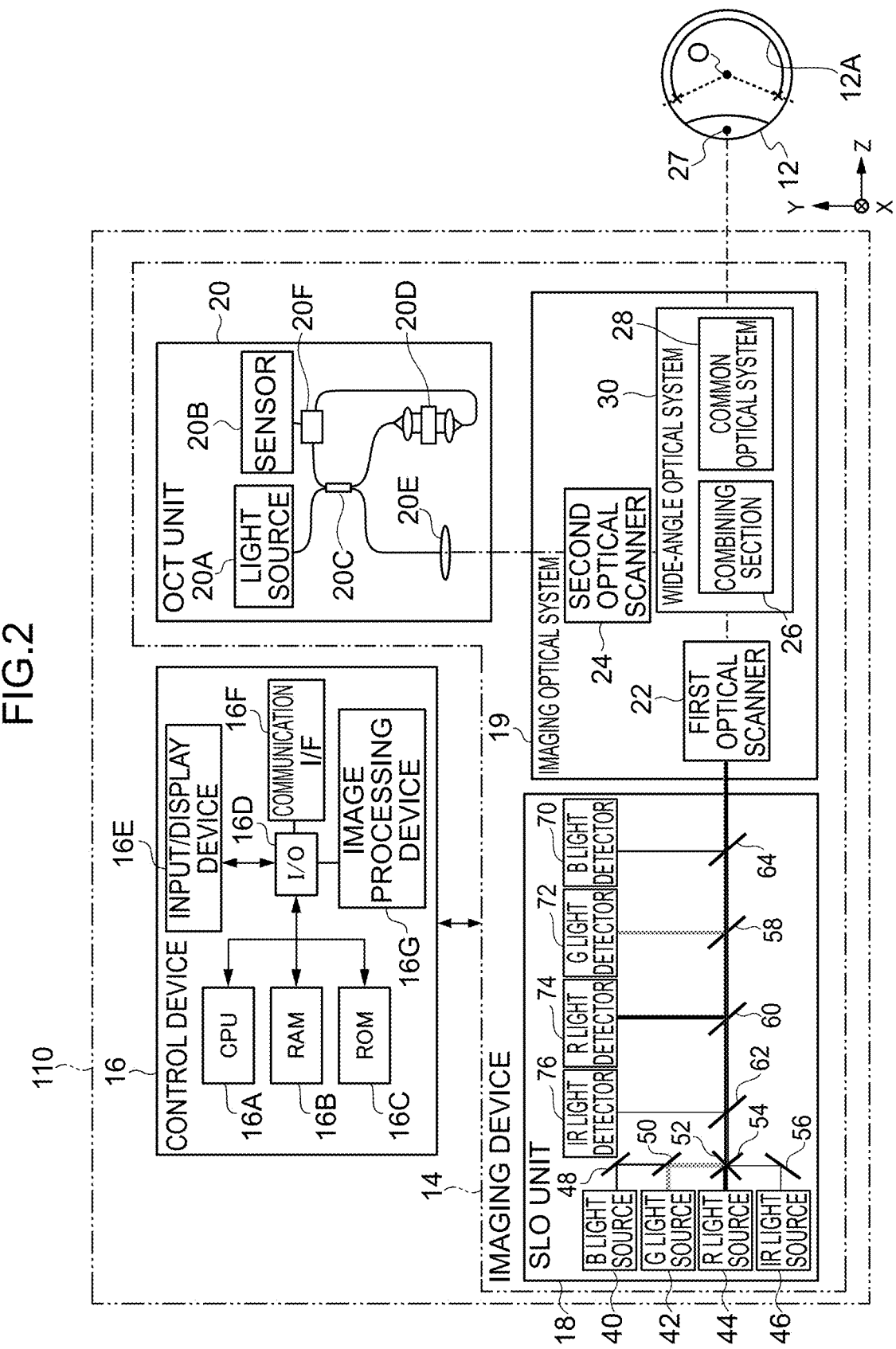
FIG. 2 is a schematic configuration diagram illustrating an overall configuration of an ophthalmic device 110.

Next, explanation follows regarding a configuration of the ophthalmic device 110, with reference to FIG. 2.

For ease of explanation, scanning laser ophthalmoscope is abbreviated to SLO. Optical coherence tomography is also abbreviated to OCT.

With the ophthalmic device 110 installed on a horizontal plane and a horizontal direction taken as an X direction, a direction perpendicular to the horizontal plane is denoted a Y direction, and a direction connecting the center of the pupil at the anterior eye portion of the examined eye 12 and the center of the eyeball is denoted a Z direction. The X direction, the Y direction, and the Z direction are thus mutually perpendicular directions.

The ophthalmic device 110 includes an imaging device 14 and a control device 16. The imaging device 14 is provided with an SLO unit 18, an OCT unit 20, and an imaging optical system 19, and acquires a fundus image of the fundus of the examined eye 12. Two-dimensional fundus images that have been acquired by the SLO unit 18 are referred to hereafter as SLO images. Tomographic images, face-on images (en-face images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E connected to the CPU 16A through the I/O port 16D. The input/display device 16E includes a graphical user interface to display images of the examined eye 12 and to receive various instructions from a user. An example of the graphical user interface is a touch panel display.

The control device 16 is provided with an image processing device 16G connected to the I/O port 16D. The image processing device 16G generates images of the examined eye 12 based on data acquired by the imaging device 14. The control device 16 is provided with a communication interface (I/F) 16F connected to the I/O port 16D. The ophthalmic device 110 is connected to the eye axial length measurement device 120, the server 140, and the viewer 150 through the communication interface (I/F) 16F and the network 130.

Although the control device 16 of the ophthalmic device 110 is provided with the input/display device 16E as illustrated in FIG. 2, the technology disclosed herein is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing processor unit that operates under the control of the CPU 16A in the control device 16. Such an image processing processor unit may display SLO images and the like based on an image signal output as an instruction by the CPU 16A.

The imaging device 14 operates under the control of the CPU 16A of the control device 16. The imaging device 14 includes the SLO unit 18, an imaging optical system 19, and the OCT unit 20. The imaging optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of deflecting light beams, they may be configured by any out of, for example, polygon mirrors, mirror galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20.

The objective optical system of the common optical system 28 may be a reflection optical system employing a concave mirror such as an elliptical mirror, a refraction optical system employing a wide-angle lens, or may be a reflection-refraction optical system employing a combination of a concave mirror and a lens. Employing a wide-angle optical system that utilizes an elliptical mirror, wide-angle lens, or the like enables imaging to be performed not only of a central portion of the fundus where the optic nerve head and macular are present, but also of the retina at the periphery of the fundus where an equatorial portion of the eyeball and vortex veins are present.

For a system including an elliptical mirror, a configuration may be adopted that utilizes an elliptical mirror system as disclosed in International Publication (WO) Nos. 2016/103484 or 2016/103489. The disclosures of WO Nos. 2016/103484 and 2016/103489 are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to a pupil 27. The internal illumination angle is the angle of illumination of a light beam shone onto the fundus, and is an angle of illumination defined with respect to an eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

An angle of 200° for the internal illumination angle is an example of a "specific value" of technology disclosed herein.

SLO fundus images obtained by imaging at an imaging angle having an internal illumination angle of 160° or greater are referred to as UWF-SLO fundus images. UWF is an abbreviation of ultra-wide field. Obviously an SLO image that is not UWF can be acquired by imaging the fundus at an imaging angle that is an internal illumination angle of less than 160°.

An SLO system is realized by the control device 16, the SLO unit 18, and the imaging optical system 19 as illustrated in FIG. 2. The SLO system is provided with the wide-angle optical system 30, enabling fundus imaging over the wide FOV 12A.

The SLO unit 18 is provided with plural light sources such as, for example, a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using reflection or transmission. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 56, 52. The respective lights are thereby guided onto a single optical path.

The SLO unit 18 is configured so as to be capable of switching between the light source or the combination of light sources employed for emitting laser light of different wavelengths, such as a mode in which G light, R light and B light are emitted, a mode in which infrared light is emitted, etc. Although the example in FIG. 2 includes four light sources, i.e. the B light source 40, the G light source 42, the R light source 44, and the IR light source 46, the technology disclosed herein is not limited thereto. For example, the SLO unit 18 may, furthermore, also include a white light source, in a configuration in which light is emitted in various modes, such as a mode in which white light is emitted alone.

Light introduced to the imaging optical system 19 from the SLO unit 18 is scanned in the X direction and the Y direction by the first optical scanner 22. The scanning light passes through the wide-angle optical system 30 and the pupil 27 and is shone onto the posterior eye portion of the examined eye 12. Reflected light that has been reflected by the fundus passes through the wide-angle optical system 30 and the first optical scanner 22 and is introduced into the SLO unit 18.

The SLO unit 18 is provided with a beam splitter 64 that, from out of the light coming from the posterior eye portion (e.g. fundus) of the examined eye 12, reflects the B light therein and transmits light other than B light therein, and a beam splitter 58 that, from out of the light transmitted by the beam splitter 64, reflects the G light therein and transmits light other than G light therein. The SLO unit 18 is further provided with a beam splitter 60 that, from out of the light transmitted through the beam splitter 58, reflects R light therein and transmits light other than R light therein. The SLO unit 18 is further provided with a beam splitter 62 that reflects IR light from out of the light transmitted through the beam splitter 60.

The SLO unit 18 is provided with plural light detectors corresponding to the plural light sources. The SLO unit 18 includes a B light detector 70 for detecting B light reflected by the beam splitter 64, and a G light detector 72 for detecting G light reflected by the beam splitter 58. The SLO unit 18 also includes an R light detector 74 for detecting R light reflected by the beam splitter 60 and an IR light detector 76 for detecting IR light reflected by the beam splitter 62.

Light that has passed through the wide-angle optical system 30 and the first optical scanner 22 and been introduced into the SLO unit 18 (i.e. reflected light that has been reflected by the fundus) is reflected by the beam splitter 64 and photo-detected by the B light detector 70 when B light, and is transmitted through the beam splitter 64 and reflected by the beam splitter 58 and photo-detected by the G light detector 72 when G light. When R light, the incident light is transmitted through the beam splitters 64, 58, reflected by the beam splitter 60, and photo-detected by the R light detector 74. When IR light, the incident light is transmitted through the beam splitters 64, 58, 60, reflected by the beam splitter 62, and photo-detected by the IR light detector 76.

The image processing device 16G that operates under the control of the CPU 16A employs signals detected by the B light detector 70, the G light detector 72, the R light detector 74, and the IR light detector 76 to generate UWF-SLO images.

The UWF-SLO image (sometimes referred to as a UWF fundus image or an original fundus image as described later) encompasses a UWF-SLO image (green fundus image) obtained by imaging the fundus in green, and a UWF-SLO image (red fundus image) obtained by imaging the fundus in red. The UWF-SLO image further encompasses a UWF-SLO image (blue fundus image) obtained by imaging the fundus in blue, and a UWF-SLO image (IR fundus image) obtained by imaging the fundus in IR.

The control device 16 also controls the light sources 40, 42, 44 so as to emit light at the same time. A green fundus image, a red fundus image, and a blue fundus image are obtained with mutually corresponding positions by imaging the fundus of the examined eye 12 at the same time with the B light, G light, and R light. An RGB color fundus image is obtained from the green fundus image, the red fundus image, and the blue fundus image. The control device 16 obtains a green fundus image and a red fundus image with mutually corresponding positions by controlling the light sources 42, 44 so as to emit light at the same time and by imaging the fundus of the examined eye 12 at the same time with the G light and R light. A RG color fundus image is obtained from the green fundus image and the red fundus image.

Specific examples of the UWF-SLO image include a blue fundus image, a green fundus image, a red fundus image, an IR fundus image, an RGB color fundus image, and an RG color fundus image. The image data for the respective UWF-SLO images are transmitted from the ophthalmic device 110 to the server 140 through the communication interface (I/F) 16F, together with patient information input through the input/display device 16E. The respective image data of the UWF-SLO image and the patient information is stored associated with each other in the storage device 254. The patient information includes, for example, patient ID, name, age, visual acuity, right eye/left eye discriminator, and the like. The patient information is input by an operator through the input/display device 16E.

An OCT system is realized by the control device 16, the OCT unit 20, and the imaging optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light to serve as measurement light, the parallel light is introduced into the imaging optical system 19. The measurement light is scanned in the X direction and the Y direction by the second optical scanner 24. The scanning light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processing device 16G operating under the control of the CPU 16A generates OCT images, such as tomographic images and en-face images, based on OCT data detected by the sensor 20B.

OCT fundus images obtained by imaging at an imaging angle having an internal illumination angle of 160° or greater are referred to as UWF-OCT images. Obviously OCT data can be acquired at an imaging angle having an internal illumination angle of less than 160°.

The image data of the UWF-OCT images is transmitted, together with the patient information, from the ophthalmic device 110 to the server 140 though the communication interface (I/F) 16F. The image data of the UWF-OCT images and the patient information is stored associated with each other in the storage device 254.

Note that although in the present exemplary embodiment an example is given in which the light source 20A is a swept-source OCT (SS-OCT), the light source 20A may be configured from various types of OCT system, such as a spectral-domain OCT (SD-OCT) or a time-domain OCT (TD-OCT) system.

Next, explanation follows regarding the eye axial length measurement device 120. The eye axial length measurement device 120 has two modes, i.e. a first mode and a second mode, for measuring eye axial length, this being the length of an examined eye 12 in an eye axial direction. In the first mode light from a non-illustrated light source is guided into the examined eye 12. Interference light between light reflected from the fundus and light reflected from the cornea is photo-detected, and the eye axial length is measured based on an interference signal representing the photo-detected interference light. The second mode is a mode to measure the eye axial length by employing non-illustrated ultrasound waves.

The eye axial length measurement device 120 transmits the eye axial length as measured using either the first mode or the second mode to the server 140. The eye axial length may be measured using both the first mode and the second mode, and in such cases, an average of the eye axial lengths as measured using the two modes is transmitted to the server 140 as the eye axial length. The server 140 stores the eye axial length of the patients in association with patient ID.

Figure 3:
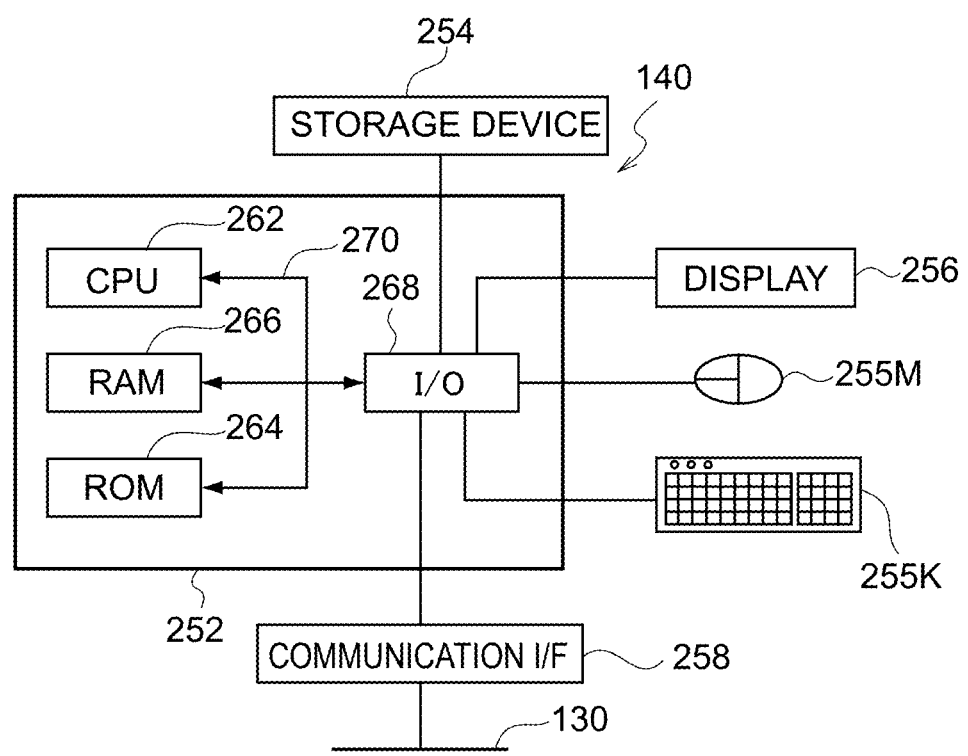
FIG. 3 is a block diagram of configuration of an electrical system of a server 140.

Explanation follows regarding a configuration of an electrical system of the server 140, with reference to FIG. 3. As illustrated in FIG. 3, the server 140 is provided with a computer body 252. The computer body 252 includes a CPU 262, RAM 266, ROM 264, and an input/output (I/O) port 268 connected together by a bus 270. The storage device 254, a display 256, a mouse 255M, a keyboard 255K, and a communication interface (I/F) 258 are connected to the input/output (I/O) port 268. The storage device 254 is, for example, configured by non-volatile memory. The input/output (I/O) port 268 is connected to the network 130 through the communication interface (I/F) 258. The server 140 is thus capable of communicating with the ophthalmic device 110 and the viewer 150. The storage device 254 is stored with an image processing program, described later. Note that the image processing program may be stored in the ROM 264.

The image processing program is an example of a "program" of technology disclosed herein. The storage device 254 and the ROM 264 are examples of "memory" and "computer readable storage medium" of technology disclosed herein. The CPU 262 is an example of a "processor" of technology disclosed herein.

A processing section 208, described later, of the server 140 (see also FIG. 5) stores various data received from the ophthalmic device 110 in the storage device 254. More specifically, the processing section 208 stores respective image data of the UWF-SLO images and image data of the UWF-OCT images in the storage device 254 associated with the patient information (such as the patient ID as described above). Moreover, in cases in which there is a pathological change in the examined eye of the patient and cases in which surgery has been performed to a pathological lesion, pathology information is input through the input/display device 16E of the ophthalmic device 110 and transmitted to the server 140. The pathology information is stored in the storage device 254 associated with the patient information. The pathology information includes information about the position of the pathological lesion, name of the pathological change, and name of the surgeon and date/time of surgery etc. when surgery was performed on the pathological lesion.

The viewer 150 is provided with a computer equipped with a CPU, RAM, ROM and the like, and a display. The image processing program is installed in the ROM, and based on an instruction from a user, the computer controls the display so as to display the medical information such as fundus images acquired from the server 140.

Figure 4:
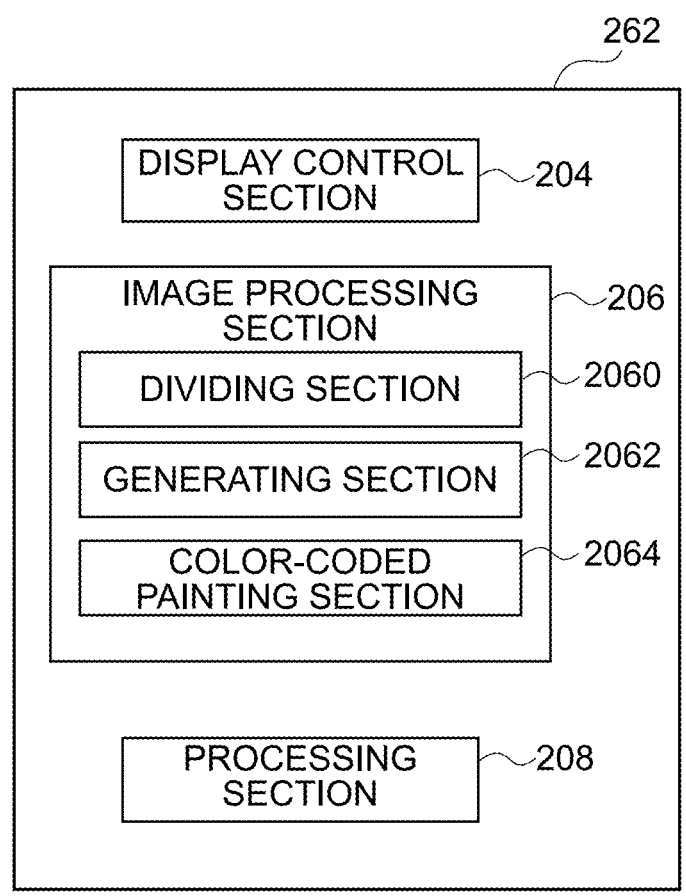
FIG. 4 is a block diagram illustrating functionality of a CPU 262 of a server 140.

Next, description follows regarding various functions implemented by the CPU 262 of the server 140 executing the image processing program, with reference to FIG. 4. The image processing program includes a display control function, an image processing function (dividing function, generation function, color-coded paint function), and a processing function. By the CPU 262 executing the image processing program including each of these functions, the CPU 262 functions as a display control section 204, an image processing section 206 (dividing section 2060, generating section 2062, color-coded painting section 2064), and the processing section 208, as illustrated in FIG. 4.

Figure 5:
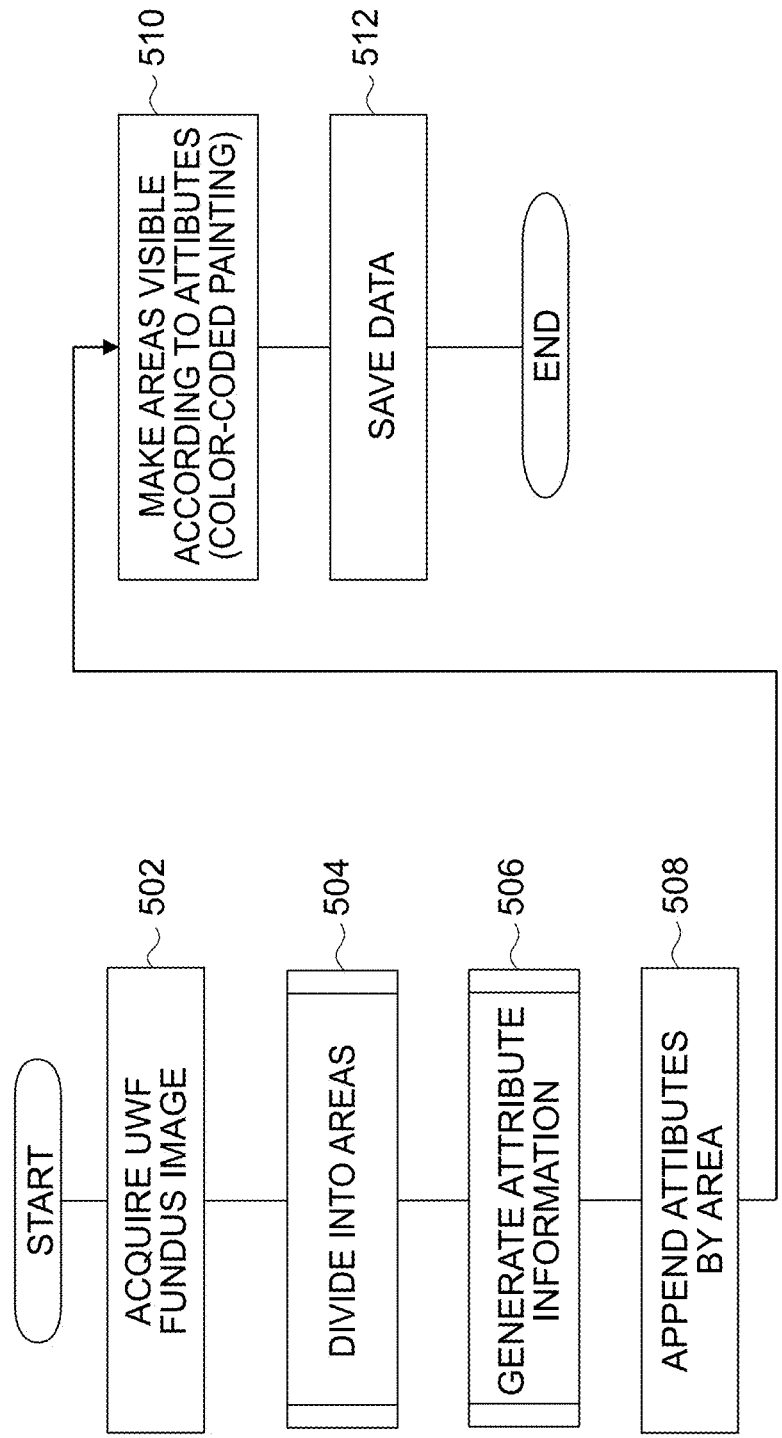
FIG. 5 is a flowchart of an image processing by the server 140.

Next detailed description follows regarding image processing by the server 140, with reference to FIG. 5. The image processing illustrated in the flowchart of FIG. 5 is implemented by the CPU 262 of the server 140 executing the image processing program. This image processing is started when a UWF fundus image (UWF-SLO image) is acquired by the ophthalmic device 110 and transmitted together with the patient ID to the server 140, and the server 140 has received the patient ID and the UWF fundus image.

At step 502 the processing section 208 acquires the UWF fundus image (original fundus image) from the storage device 254. The processing section 208 acquires, for example, a red fundus image, a green fundus image, and a RGB color fundus image.

At step 504 the image processing section 206 divides the fundus region of the UWF fundus image into plural areas including at least a first area and a second area, and at step 506 the image processing section 206 generates attribute information for each of the areas.

In the technology disclosed herein there are plural different types of processing applicable for the area division processing of step 504. For example, there is a first processing in which the blood vessels are used as area boundaries, there is a second processing in which watersheds of the choroidal vascular network are used as area boundaries, and the like. Note that the first processing is adopted for the area division processing of step 504 of the present exemplary embodiment. The second processing is adopted for the area division processing of step 504 of the second exemplary embodiment, as described later.

Figure 6:
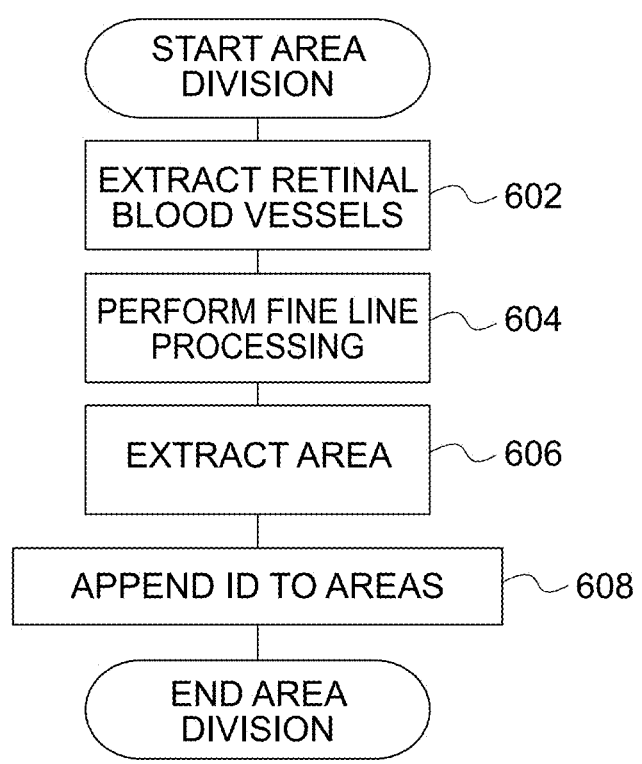
FIG. 6 is a flowchart of area division processing of step 504 of FIG. 5.

Explanation follows regarding the first processing in which blood vessel are used as area boundaries, with reference to FIG. 6.

At step 602 the dividing section 2060 extracts retinal blood vessels from the green fundus image of the UWF fundus image. The reason the green fundus image is employed is because green light (having a wavelength corresponding to green) reaches to a depth where the retina of the fundus is positioned, and so is appropriate for making structure of the retina visible. The retinal blood vessel are made visible as black in the green fundus image. This is because the retinal blood vessel absorb this light.

More specifically, the dividing section 2060 generates a retinal vascular image by extracting, as retinal blood vessel sections, areas in the green fundus image that include pixels having pixel values smaller than those of peripheral pixels. More specifically, the dividing section 2060 performs black hat processing on the green fundus image. Black hat processing is processing to subtract an original image from an image that has been subjected to closing, and means processing to extract locations of dust and noise in the original image as white dots. The locations of the pixels of the retinal blood vessels, which are black pixels, are extracted as white pixels by performing the black hat processing on the green fundus image. Namely, a retinal blood vessel image is generated that is a binarized image in which retinal blood vessel sections are white pixels and other areas are black pixels.

At step 604 the dividing section 2060 performs fine line processing by finding a center line of the retinal blood vessel regions in the retinal vascular image. More specifically, the dividing section 2060 forms fine lines by performing fine line processing (processing to make lines fine by using a Hildich method or the like so that only one pixel remains on the center line in the binarized images) on the retinal vascular image. An image (skeleton image) is obtained in which the retinal blood vessels illustrated in FIG. 8 have been made into fine lines. The center lines are displayed as white pixels due to performing the fine line processing on the skeleton image.

At step 606, the dividing section 2060 takes the skeleton image (see FIG. 8) and divides it into (extracts) plural areas including at least a first area and a second area.

Figure 8:
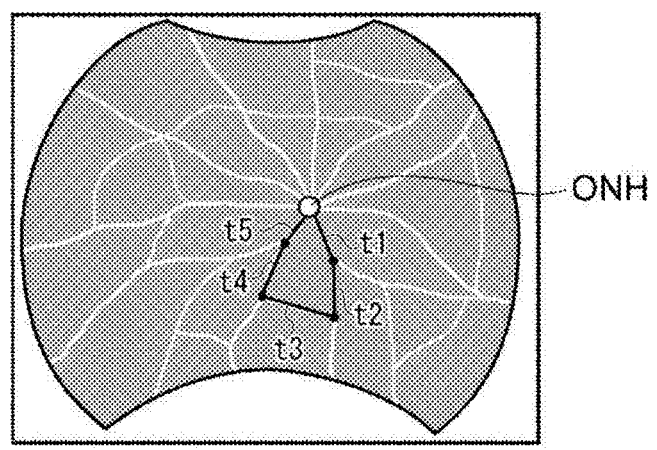
FIG. 8 is a diagram illustrating a portion of a retinal vascular image closed by blood vessel image sections.

More specifically the dividing section 2060 divides the center line of the retinal blood vessels in the skeleton image into plural sections. FIG. 8 illustrates an example in which an area has been divided below the optic nerve head (ONH in FIG. 8) of the skeleton image. This division is by extracting branch points and merge points (black dots and a circle mark indicating the ONH in FIG. 8).

Next the dividing section 2060 extracts, as sections, line segments of a center line defined by one branch point and another branch point. FIG. 8 illustrates a manner in which five sections from t1 to t5 have been extracted.

Figure 9:
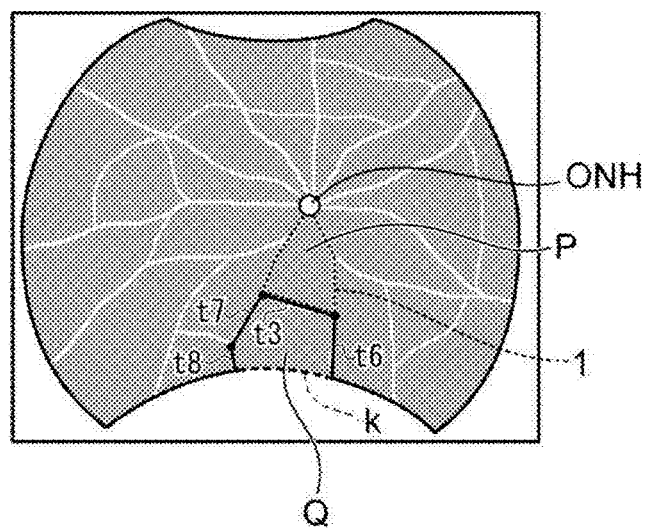
FIG. 9 is a diagram illustrating a portion not closed by blood vessel image sections, but closed by blood vessel image sections and by a boundary between a retinal vascular image and a background region.

The dividing section 2060 extracts an area surrounded by plural sections. In FIG. 9 the area P surrounded by sections t1, t2, t3, t4, t5 has been extracted. The dividing section 2060 also sets an outline line 1 indicating the outline of the area P. The dividing section 2060 completes processing to divide the skeleton image into plural areas by performing extraction of sections, extraction of areas, and setting of outline lines in this manner for the entire skeleton image.

However, there are areas present in the skeleton image not closed by sections corresponding to blood vessels of the fundus. For example, as illustrated in FIG. 9, there is an area Q present that is surrounded in one part of its outline by sections t6, t3, t7, 18, but the remaining section of the outline is not outline originating from blood vessels, namely, is a section k of a peripheral edge of the skeleton image (a section of boundary between the background region and the fundus region).

Figure 10:
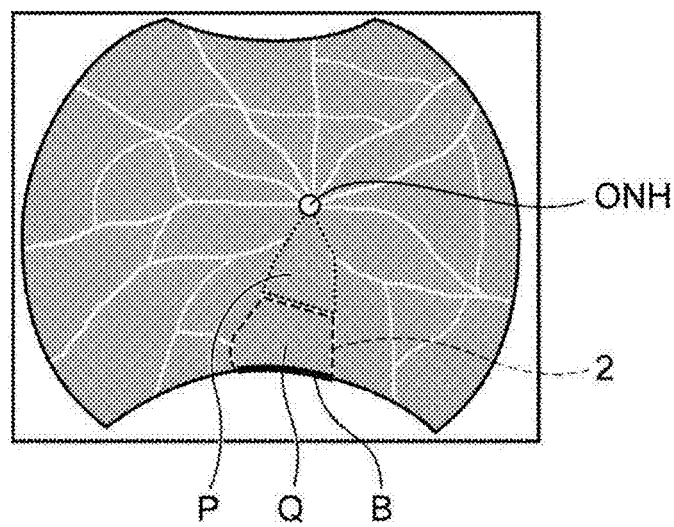
FIG. 10 is a diagram illustrating a manner in which an outline line is set at a boundary between a retinal vascular image and a background region at a portion not closed by blood vessel image sections.

In such cases the dividing section 2060 forcibly recognizes the section k as being part of the outline. The sum of the outline line corresponding to the sections t6, t3, t7, 18 and the outline line formed by section k as illustrated in FIG. 9 is extracted as an outline line 2 of the area Q, as illustrated in FIG. 10. The dividing section 2060 performs dividing to give the area Q set by the outline line 2. Such areas where a peripheral edge of the skeleton image is part of the outline are recognized as fundus peripheral areas (areas with the attribute fundus periphery).

Figure 11:
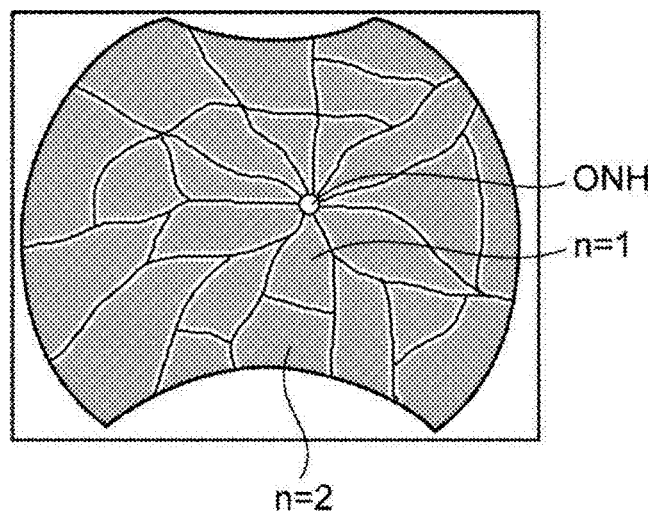
FIG. 11 is a diagram illustrating a manner in which identification information is appended to plural areas.

At step 608 the dividing section 2060 appends identification information to each of the extracted areas. For example, as illustrated in FIG. 11, the dividing section 2060 appends n=1 as the identification information (ID) to the area P, and appends n=2 as the identification information (ID) to the separate area Q.

Figure 7:
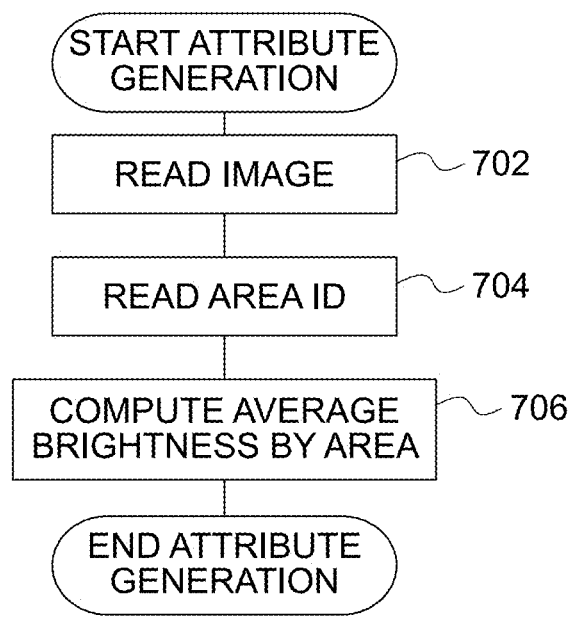
FIG. 7 is a flowchart of attribute information generation processing of step 506 of FIG. 6.

When the identification information appending processing of step 608 is finished, the area division processing of step 504 of FIG. 5 is ended, and image processing transitions to attribute information generation processing of step 506 (see FIG. 7).

At step 702 of FIG. 7, the generating section 2062 reads a UWF fundus image (for example, a RGB color fundus image), and at step 704 the generating section 2062 reads the area identification information (ID).

At step 706 the generating section 2062 computes an average brightness of each area as the attribute information. More specifically, the generating section 2062 sets a variable n, which is the area identification information, to 0, and increments the variable n by 1. The generating section 2062 acquires plural pixel values of a portion of the UWF fundus image corresponding to the area identified by variable n, and computes the average brightness of the area n based on the plural pixel values acquired. The generating section 2062 repeatedly computes the average brightness of the area n until variable n reaches the total number of areas N. Thus the average brightness is computed as attribute information for each of all of the areas.

The respective average brightness for all of the areas is fundus physical information corresponding to the areas, more specifically is fundus optical information corresponding to the area (for example, "information related to a reflectivity of light"), and is an example of "first attribute information" and "second attribute information" of the technology disclosed herein. More specifically, the average brightness of the area P closed by blood vessel image sections from t1 to t5 illustrated in FIG. 9 are an example of the "first attribute information" of technology disclosed herein. Moreover, the average brightness of the area Q2 closed by the blood vessel image sections corresponding to blood vessels of the fundus as illustrated in FIG. 9 and by the boundary section between the fundus region and the background image as illustrated in FIG. 10, is an example of the "second attribute information" of technology disclosed herein.

Other examples of attribute information that may be employed include, instead of the average brightness of each area, a maximum brightness value, a minimum brightness value, a difference, quotient, or product of the maximum brightness value and the minimum brightness value, for the pixel values of each area.

Another example of attribute information that may be employed is a rank of average brightness range. This is, more specifically, the following. A low average brightness first range is predetermined as rank 1, and a second range of average brightness higher than that of the first range is predetermined as rank 2, and these are employed as average brightness range ranks. The generating section 2062 determines which rank each area falls in out of rank 1 or rank 2 from its average brightness. The generating section 2062 associates information indicating belonging to rank 1 to an area whose average brightness falls in the first range. The generating section 2062 associates information indicating belonging to rank 2 to an area whose average brightness falls in the second range. The information indicating belonging to rank 1 and the information indicating belonging to rank 2 are examples of "attribute information" of technology disclosed herein.

Furthermore, the generating section 2062 computes thicknesses of a retinal nerve fiber layer (RNFL) and a choroid layer for each area. Note that the thicknesses of these layers are generated based on the OCT data. Segmentation is performed on the tomographic image, and each layer of the retina, such as the retinal nerve fiber layer and the choroid layer, is identified. Average values are found for the thicknesses of the retinal nerve fiber layer and the choroid layer for each of the areas. The average value of the thicknesses of the retinal nerve fiber layer and of the choroid layer for each area are examples of attribute information, and are examples of "information related to a layer thickness of a fundus" of technology disclosed herein.

Instead of the average value of the thickness of each of the layers, a maximum value, a minimum value, a difference, quotient, or product of the maximum value and minimum value, for the layer thickness of each of the areas, or a combination thereof, may be employed as the attribute information.

However, in the plural areas described above, there may be abnormal areas as well as normal areas. The normal areas include, for example, a first attribute indicating an attribute of normal. The abnormal areas include, for example, a second attribute indicating an attribute of abnormal. The abnormal areas include, for example, areas of pathological change or non perfusion areas (NPA).

The non perfusion areas (NPAs) are fundus regions where there is no blood flow or hardly any blood flow in the fundus due to retina capillary vascular bed obstruction, or due to impaired blood flow or the like resulting from a disorder of the retinal blood vessels or the choroidal blood vessels. They may also be avascular areas (AVAs) which are areas on a fundus where there are no blood vessels or only sparse blood vessels.

The non perfusion areas are detected by extracting plural pixels in the retinal vascular image darker than a first darkness, and by detecting areas having a surface area of a specific surface area or greater of contiguous dark pixels of the first darkness or lower in the plural pixels extracted. The method described in International Publication (WO) No. 2019/130583 may be employed as a method for extraction and detection of the non perfusion areas. The disclosure of WO No. 2019/130583 of the international publication of Jul. 4, 2019 is incorporated in its entirety into the present specification by reference herein.

The first attribute indicating an attribute of normal may be employed as the attribute information when the area is a normal area, and the second attribute indicating attribute of abnormal may be employed as the attribute information when the area is an abnormal area. A normal fundus region is an example of a "first area" of technology disclosed herein, and an abnormal fundus region is an example of a "second area" of technology disclosed herein.

When average brightness saving processing of step 706 has finished, the attribute information generation processing of step 506 of FIG. 5 is ended, and the image processing transitions to attribute appending processing of step 508.

At step 508 the processing section 208 appends an attribute to each of the areas identified by the variable n. More specifically, the processing section 208 associates the variable n with the attribute information, such as the average brightness, and stores the attribute information in the storage device 254.

When the attribute appending processing of step 508 has finished, the image processing transitions to step 510. At step 510 the color-coded painting section 2064 creates visibility data to make the areas visible according to area attributes.

Explanation follows regarding visibility data for a case in which the average brightness has been computed as the attribute information. Note that a manner in which each of the areas is made visible based on the visibility data will be described in detail later, and is illustrated in the area overlay UWF fundus image display field 1032B of FIG. 12.

First the range of possible average brightness D0 to D256 is divided into plural brightness ranges. For example, the brightness D0 to D256 may be divided into plural ranges such as a first brightness range K1 to a fourth brightness range K4. For example, the first brightness range K1 is from brightness D256 to D192, the second brightness range K2 is from brightness D192 to D128, the third brightness range K3 is from brightness D128 to D64, the fourth brightness range K4 is from brightness D64 to D0. Note that there is no limit to there being 4 brightness ranges, and there may be 2, 3, 5, 6, or so thereof.

Each of the brightness ranges is associated with a corresponding mutually different color. For example, the first brightness range K1 is associated with yellow, the second brightness range K2 is associated with orange, the third brightness range K3 is associated with green, and the fourth brightness range K4 is associated with blue.

At step 510 the color-coded painting section 2064 reads the average brightness for each area from the storage device 254. The color-coded painting section 2064 determines which range the read average brightness falls in from the first brightness range K1 to the fourth brightness range K4, and identifies the color information associated with the determined brightness range the average brightness falls in.

An instruction is then given to use the color information to make the display mode of the areas display in a color mode, as described later. The color information is an example of a "first mode instruction information" and a "second mode instruction information" of technology disclosed herein. More specifically, the color information identified as being associated with the average brightness of the area P closed by the blood vessel image sections t1 to t5 illustrated in FIG. 9 is an example of the "first mode instruction information" of technology disclosed herein. Moreover, the color information identified as being associated with average brightness of the area Q2 illustrated in FIG. 10 closed by the blood vessel image sections corresponding to the blood vessels of the fundus and by the boundary section between the fundus region and the background image, is an example of the "second mode instruction information" of technology disclosed herein.

An ophthalmologist inputs the patient ID into the viewer 150 when examining the examined eye of the patient. The viewer 150 instructs the server 140 to transmit image data for the examined eye corresponding to the patient ID. The server 140 transmits the patient name, patient age, patient visual acuity, left eye/right eye information, eye axial length, imaging date, and image data corresponding to the patient ID to the viewer 150 together with the patient ID.

The image data and the like includes the UWF fundus image, the retinal vascular image, the choroidal vascular image, and position information, identification information, average brightness, and color information for each of the various areas.

Figure 12:
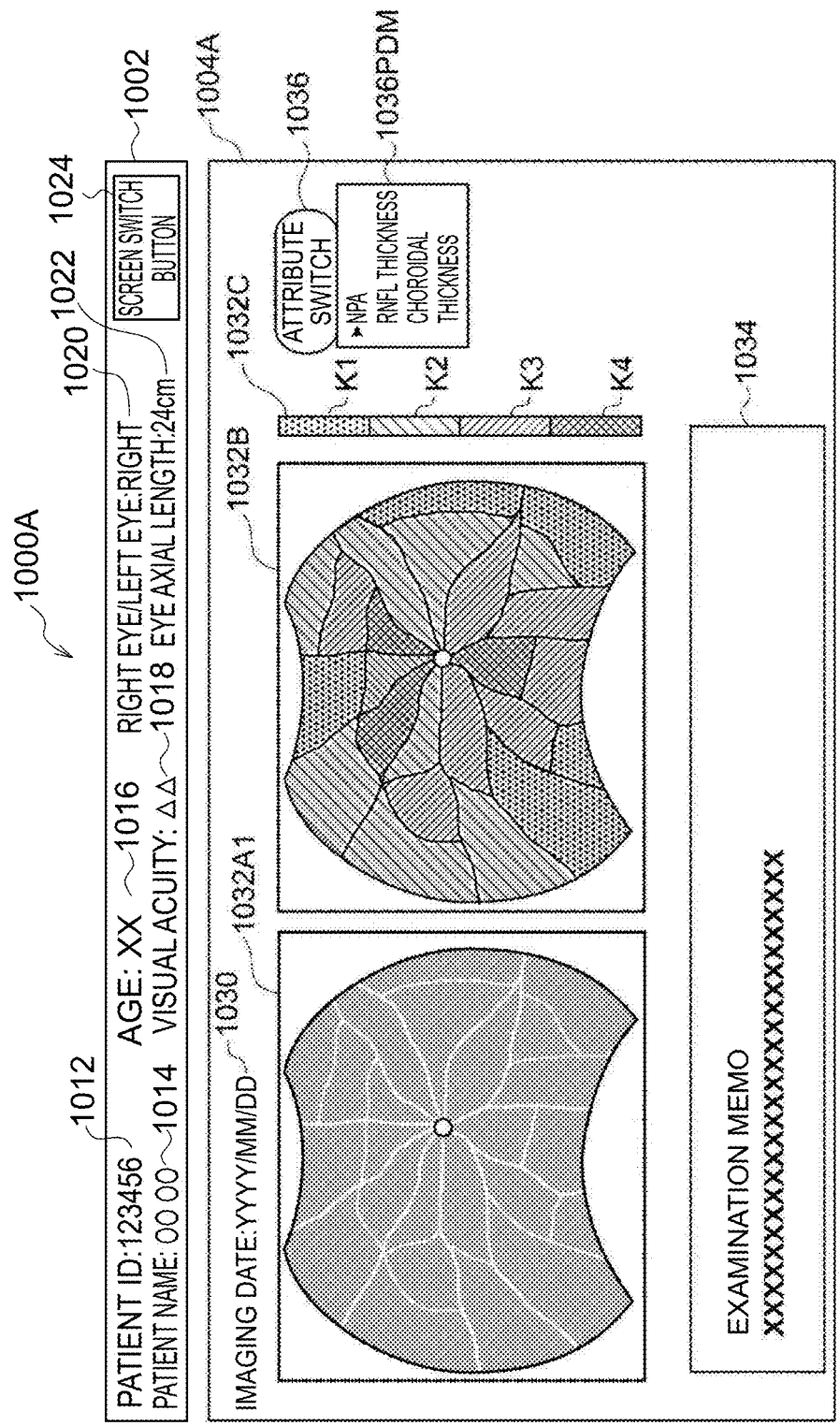
FIG. 12 is a diagram illustrating a first fundus image display screen 1000A.

On receiving the patient ID, patient name, patient age, patient visual acuity, left eye/right eye information, eye axial length, imaging date, and image data, the viewer 150 displays a first fundus image display screen 1000A illustrated in FIG. 12 on a display.

As illustrated in FIG. 12, the first fundus image display screen 1000A includes a patient information display field 1002 and a first fundus image information display field 1004A.

The patient information display field 1002 is for displaying the patient ID, the patient name, the patient age, the visual acuity of the patient, left eye/right eye information, and eye axial length, and includes display fields from 1012 to 1022, and a screen switch button 1024. The received patient ID, patient name, patient age, patient visual acuity, left eye/right eye information, and eye axial length are displayed in the display fields from 1012 to 1022.

The first fundus image information display field 1004A includes an imaging date display field 1030, a UWF fundus image display field 1032A1, an area overlay UWF fundus image display field 1032B, a brightness range color display field 1032C, an information display field 1034, and an attribute switch button 1036.

The imaging date (YYYY/MM/DD) is displayed in the imaging date display field 1030. Comments and memos during examination by a user (ophthalmologist) are displayed as text in the information display field 1034.

The original UWF fundus image is displayed in the UWF fundus image display field 1032A1.

Note that a retinal vascular image or a skeleton image may also be displayed.

Initially there is no image displayed in the area overlay UWF fundus image display field 1032B.

The attribute switch button 1036 is a button to select an image to display on the area overlay UWF fundus image display field 1032B. When the attribute switch button 1036 is operated the pull down menu 1036PDM is displayed. The pull down menu 1036PDM is, for example, a menu of 3 items: "NPA", "RNFL thickness", and "choroidal thickness".

"NPA" instructs an image to be displayed in the area overlay UWF fundus image display field 1032B in which non perfusion areas (NPA) are overlaid on the original UWF fundus image.

"RNFL thickness" instructs an image to be displayed in the area overlay UWF fundus image display field 1032B in which the non perfusion areas (NPA) are overlaid on the UWF fundus image and the RNFL thickness display is enabled.

"Choroidal thickness" instructs an image to be displayed in the area overlay UWF fundus image display field 1032B in which the non perfusion areas (NPA) are overlaid on the UWF fundus image and the choroidal thickness display is enabled.

FIG. 12 illustrates content of a screen when "NPA" has been selected on the pull down menu 1036PDM. An image is displayed in the area overlay UWF fundus image display field 1032B in which the non perfusion areas (NPA) are overlaid on the UWF fundus image.

The color information is associated with the identification information for each of the areas, and so in the area overlay UWF fundus image display field 1032B the overlaid areas are displayed in the color indicated by the color information.

When "RNFL thickness" has been selected on the pull down menu 1036PDM, the viewer 150 displays in the area overlay UWF fundus image display field 1032B an image in which the non perfusion areas (NPA) are overlaid on the UWF fundus image and the RNFL thickness display is enabled.

When "choroidal thickness" has been selected on the pull down menu 1036PDM, the viewer 150 displays in the area overlay UWF fundus image display field 1032B an image in which the non perfusion areas (NPA) are overlaid on the UWF fundus image and the choroidal thickness display is enabled.

Figure 13:
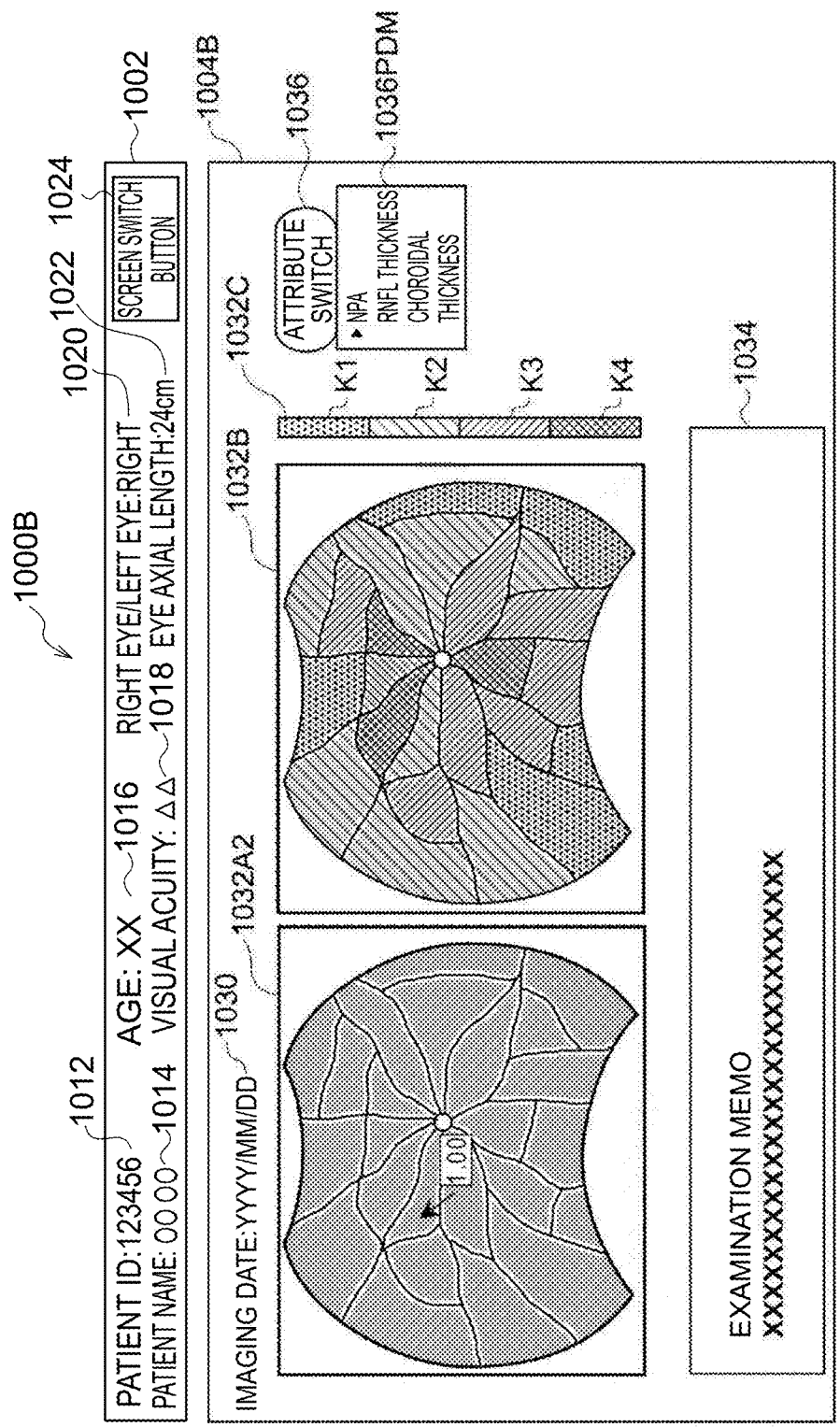
FIG. 13 is a diagram illustrating a second fundus image display screen 1000B.

In cases in which the screen switch button 1024 of FIG. 12 has been operated, the viewer 150 displays a second fundus image display screen 1000B illustrated in FIG. 13 on the display.

The content of the first fundus image display screen 1000A and the second fundus image display screen 1000B is substantially similar and so the same reference numerals are appended to the same parts, explanation thereof will be omitted, and explanation will focus on the differing parts alone.

The second fundus image display screen 1000B includes, instead of the UWF fundus image display field 1032A1 of FIG. 12, a UWF fundus image display field 1032A2 to display an image of the non perfusion areas (NPA) overlaid on the UWF fundus image.

In a UWF fundus image display field 1032A2, a non perfusion area (NPA) overlaid on the UWF fundus image is selected by aligning a cursor (see arrow) therewith, and the viewer 150 displays the average brightness of the selected area (for example, 1.00) corresponding to the cursor.

As described above, in the present exemplary embodiment the fundus region of the ultra-wide field fundus image is divided into plural areas including at least a first area and a second area, and the first attribute information indicating the attribute of the first area and the second attribute information indicating the attribute of the second area are generated. The first mode instruction information to instruct display in the first mode in which the first area is associated with the first attribute information, and the second mode instruction information to instruct display in the second mode in which the second area is associated with the second attribute information, are generated. The first area is displayed by the first mode instructed by the first mode instruction information, and the second area is displayed by the second mode instructed by the second mode instruction information. This accordingly enables a distinction to be ascertained between a state of each of the areas on the fundus and the state of other areas.

Next, detailed explanation follows regarding a second exemplary embodiment of the present invention. The configuration of the second exemplary embodiment is similar to the configuration of the first exemplary embodiment, and so the same reference numerals are appended to same parts, and explanation thereof will be omitted.

Next, explanation follows regarding image processing in the second exemplary embodiment. As described above, the second exemplary embodiment differs from the first exemplary embodiment in the content of the area division processing of step 504 and the attribute information generation processing of step 506 as follows.

Figure 14:
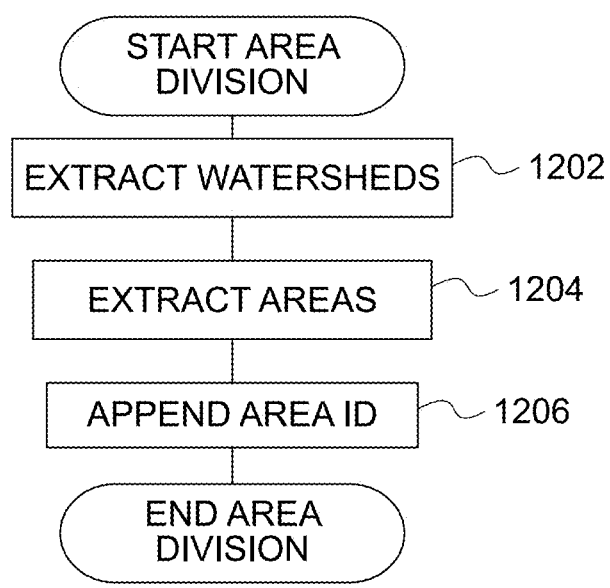
FIG. 14 is a flowchart of another example of area division processing of step 504 of FIG. 5.

FIG. 14 illustrates a flowchart of the area division processing of step 504 of the second exemplary embodiment.

At step 1202 the dividing section 2060 extracts watersheds in a choroidal vascular network. Explanation follows regarding the watershed extraction processing of step 1202.

Figure 16:
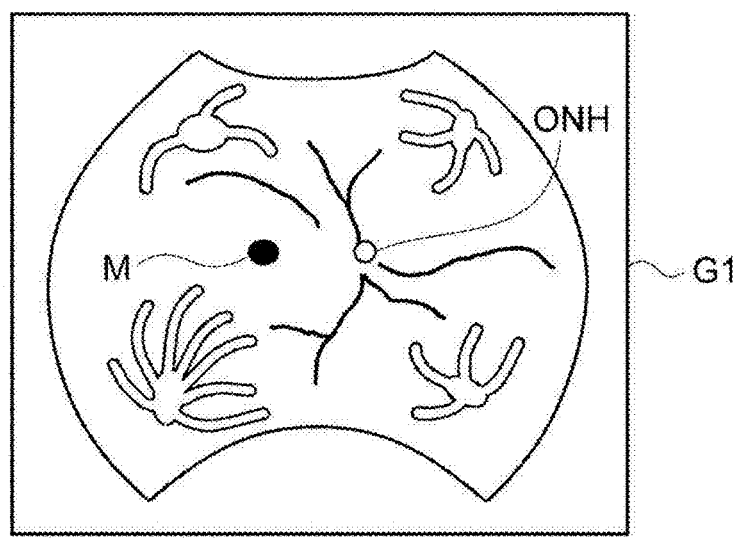
FIG. 16 is a diagram illustrating a UWF fundus image G1.

The dividing section 2060 acquires a UWF fundus image G1 (original fundus image, more specifically a red fundus image and a green fundus image (see FIG. 16)) from the storage device 254.

The dividing section 2060 generates a choroidal vascular image in the following manner.

First explanation follows regarding information included in the red fundus image and the green fundus image.

The structure of an eye is one in which a vitreous body is covered by plural layers of differing structure. The plural layers include, from the vitreous body at the extreme inside to the outside, the retina, the choroid, and the sclera. R light passes through the retina and reaches the choroid. The red fundus image therefore includes information relating to blood vessels present within the retina (retinal blood vessels) and information relating to blood vessels present within the choroid (choroidal blood vessels). In contrast thereto, G light only reaches as far as the retina. The green fundus image accordingly only includes information relating to the blood vessels present within the retina (retinal blood vessels).

Figure 17:
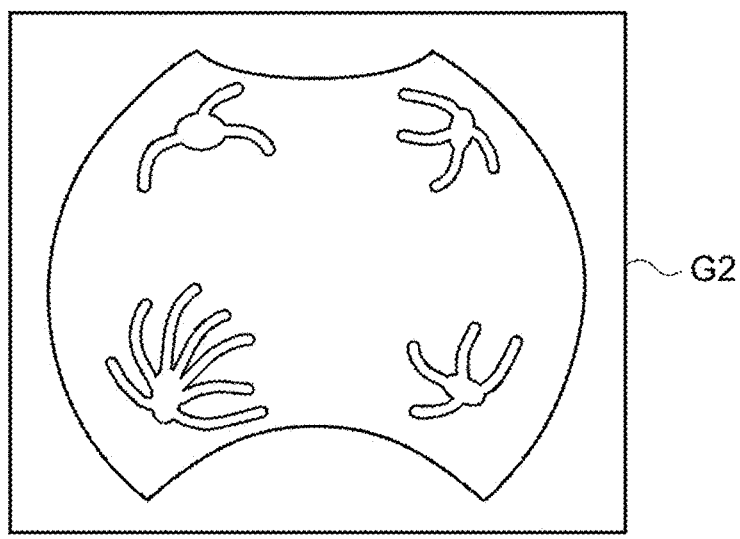
FIG. 17 is a diagram illustrating a choroidal vascular image G2.

The dividing section 2060 extracts the retinal blood vessels from the green fundus image by applying black hat filter processing to the green fundus image. Next, the dividing section 2060 removes the retinal blood vessels from the red fundus image by performing in-painting processing thereon using the retinal blood vessels extracted from the green fundus image. Namely, position information for the retinal blood vessels extracted from the green fundus image is employed when performing processing to infill the retinal blood vessel structure in the red fundus image using pixel values the same as those of surrounding pixels. The dividing section 2060 then emphasizes the choroidal blood vessels in the red fundus image by performing contrast limited adaptive histogram equalization (CLAHE) processing on the image data of the red fundus image from which the retinal blood vessels have been removed. A choroidal vascular image G2 such as illustrated in FIG. 17 is obtained in this manner. The generated choroidal vascular image is stored in the storage device 254.

The generation of the choroidal vascular image from the red fundus image and the green fundus image may be performed by the dividing section 2060 generating a choroidal vascular image using the red fundus image red fundus image or IR fundus image imaged with IR light.

A method to generate choroidal fundus images is disclosed in Japanese Patent Application No. 2018-052246 filed Mar. 20, 2018, the entirety of which is incorporated in the present specific by reference herein.

The dividing section 2060 detects the respective positions of the macular M and the optic nerve head ONH. First the dividing section 2060 reads the choroidal vascular image G2 and the green fundus image from the storage device 254.

The macular is a dark area of the green fundus image. The dividing section 2060 detects as the position of the macular an area of a specific number of pixels having the smallest pixel value in the read green fundus image.

The dividing section 2060 detects a position of the optic nerve head ONH in the green fundus image. More specifically, the dividing section 2060 performs pattern matching of a predetermined optic nerve head ONH image against the read green fundus image, and detects the optic nerve head ONH in the green fundus image. Moreover, the optic nerve head ONH is the brightest area in the green fundus image, and so an area of a specific number of pixels having the largest pixel value in the read green fundus image may be detected as the position of the optic nerve head ONH.

The choroidal vascular image is created by processing the red fundus image and the green fundus image obtained by simultaneously scanning the fundus with R light and G light. Thus when the coordinate system of the green fundus image is overlaid on the coordinate system of the choroidal vascular image, the respective positions in the green fundus image coordinate system are the same as the respective positions in the choroidal vascular image coordinate system. The respective positions on the choroidal vascular image corresponding to the positions of the macular M and the optic nerve head ONH detected in the green fundus image are therefore the respective positions of the macular and the optic nerve head.

Thus the positions of the macular and the optic nerve head may be detected in this manner from the choroidal vascular image instead of the green fundus image.

Figure 18:
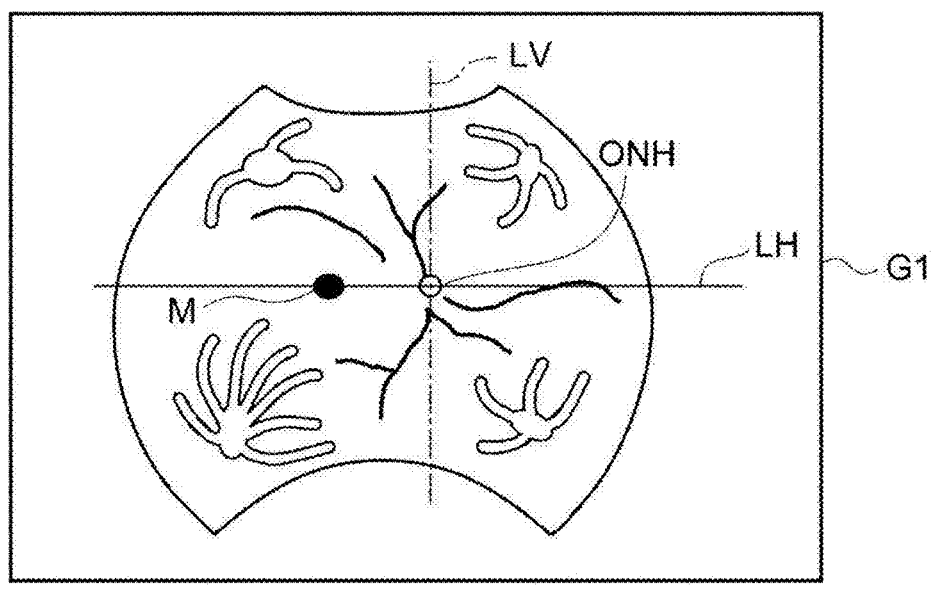
FIG. 18 is a diagram illustrating a UWF fundus image G1 set with a line LH passing through an optic nerve head ONH and a macular M and with a line LV perpendicular to the line LH.

As illustrated in FIG. 18, the dividing section 2060 sets as a first watershed LH a line LH in the UWF fundus image G1 connecting the position of the macular M and the position of the optic nerve head ONH, and detects as a second watershed LV a line LV perpendicular to the line LH and passing through the position of the optic nerve head ONH.

The watersheds are areas where the density of choroidal blood vessels is lower than other areas (areas where there are fewer choroidal blood vessels than the average density of choroidal blood vessels). There are generally four vortex veins in a normal eye, and the area of the line LH connecting the position of the macular M and the position of the optic nerve head ONH, and the area of the line LV perpendicular to the line LH and passing through the position of the optic nerve head ONH, are areas having a low density of choroidal blood vessel.

Thus in the present exemplary embodiment the line LH is detected as a first watershed, and the line LV is defined as the second watershed. Note that in the technology disclosed herein the dividing section 2060 divides the choroidal vascular image into plural areas, detects the density of choroidal blood vessels for each of the areas, and extracts the watersheds by following the areas of lower density. Furthermore, in the present disclosure, the dividing section 2060 may detect the running direction of the choroidal blood vessels, detect areas having the same direction for the running direction of the choroidal blood vessels, and extract boundaries of the detected areas as the watersheds.

Furthermore, the dividing section 2060 detects vortex veins from the choroidal vascular image G2 (see FIG. 17).

The vortex veins are flow path flow paths of blood flow flowing into the choroid, and there are from four to six vortex veins present toward the posterior pole of an equatorial portion of the eyeball. The vortex vein positions are detected based on the running direction of the choroidal blood vessels obtained by analyzing the choroidal vascular image.

The dividing section 2060 sets a movement direction (blood vessel running direction) for each of the choroidal blood vessels in the choroidal vascular image. More specifically, first the dividing section 2060 executes the following processing on each pixel in the choroidal vascular image. Namely, for each pixel the dividing section 2060 sets an area (cell) having the respective pixel at the center, and creates a histogram of brightness gradient direction at each of the pixels in the cells. Next, the dividing section 2060 takes the gradient direction having the lowest count in the histogram of the cells as the movement direction for the pixels in each of the cells. This gradient direction corresponds to the blood vessel running direction. Note that the reason for taking the gradient direction having the lowest count as the blood vessel running direction is as follows. The brightness gradient is smallest in the blood vessel running direction, whereas the brightness gradient is large in other directions (for example, there is a large difference in brightness between blood vessel and non-blood vessel tissue). Thus creating a histogram of brightness gradient for each of the pixels results in a smaller count for the blood vessel running direction. The blood vessel running direction at each of the pixels in the choroidal vascular image is set by the processing described above.

The dividing section 2060 sets an initial position of M (natural number)× N (natural number) (=L) individual hypothetical particles. More specifically, the dividing section 2060 sets a total of L initial positions at uniform spacings on the choroidal vascular image, with M positions in the vertical direction, and N positions in the horizontal direction.

Figure 19:
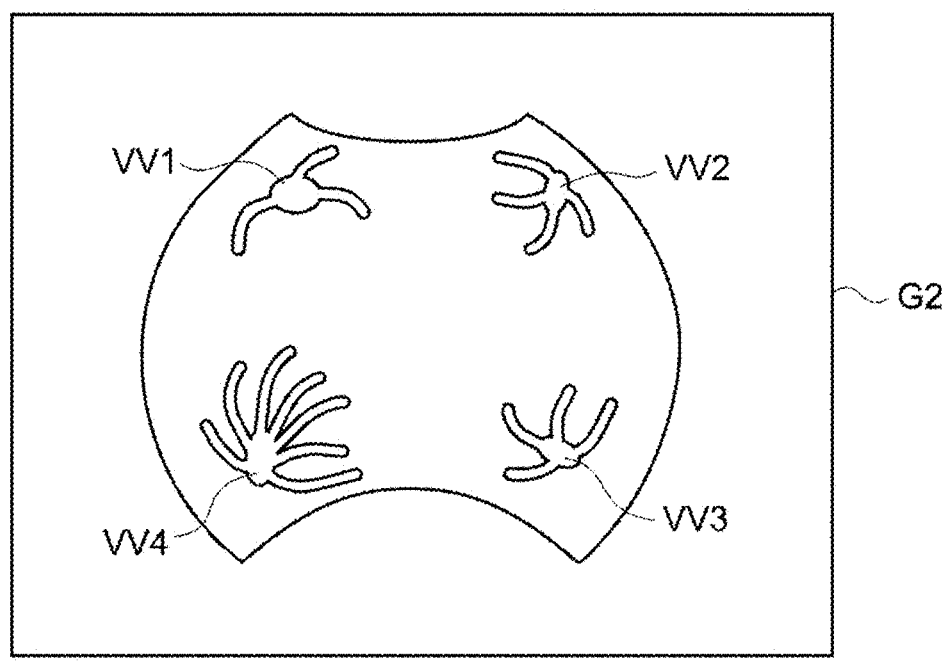
FIG. 19 is a diagram illustrating a manner in which positions of four vortex veins have been detected.

The dividing section 2060 estimates the position of the vortex veins. More specifically, the dividing section 2060 performs the following processing for each of the L positions. Namely, the dividing section 2060 acquires a blood vessel running direction at an initial position (one of the L positions), moves the hypothetical particle by a specific distance along the acquired blood vessel running direction, then re-acquires the blood vessel running direction at the moved-to position, before then moving the hypothetical particle by the specific distance along this acquired blood vessel running direction. Moving by the specific distance along the blood vessel running direction in this manner is repeated for a pre-set number of movement times. The above processing is executed for all the L positions. Points where a fixed number of the hypothetical particles or greater have congregated at this point in time are taken as the position of a vortex vein. A detected state of four vortex veins VV1 to VV4 is illustrated in FIG. 19. The bulging portions of the vortex veins (portions where plural choroidal blood vessels merge, positions of the vortex veins found from the blood vessel running directions as described above) and choroidal blood vessels connected to the bulging portions are depicted distorted in FIG. 19.

The positional information of the vortex veins (number of vortex veins, coordinates on the choroidal vascular image, etc.) are stored in the storage device 254. A method disclosed in Japanese Patent Application No. 2018-080273 and a method disclosed in WO No. PCT/JP2019/016652 may be employed as the method for detecting vortex veins. The disclosures of Patent Application No. 2018-080273 filed in Japan on Apr. 18, 2018 and WO No. PCT/JP2019/016652 filed Internationally on Apr. 18, 2019 are incorporated in their entirety in the present specification by reference herein.

When the above processing is finished, the watershed extraction processing of step 1202 is ended, and the area division processing transitions to step 1204.

Figure 20:
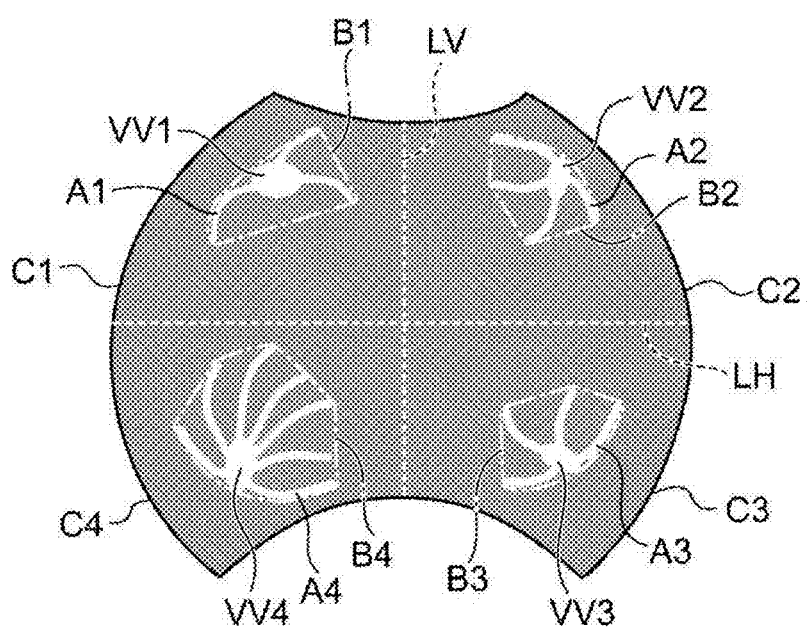
FIG. 20 is a diagram illustrating a manner in which a choroidal vascular image is divided into plural areas with respect to watersheds.

At step 1204 the dividing section 2060 divides the choroidal vascular image into plural areas with the watersheds as boundaries. In other words, the choroidal vascular image is divided so as to each include one vortex vein. As illustrated in FIG. 20, the watershed LH and the watershed LV divide to give an area C1 (a top left area including the vortex vein VV1), an area C2 (a top right area including the vortex vein VV2), an area C3 (a bottom right area including the vortex vein VV3), and an area C4 (a bottom left area including the vortex vein VV4). FIG. 20 is for a choroidal vascular image for a case in which there are four vortex veins, and so the choroidal vascular image is divided by the watersheds into four areas, the same number as the number of vortex veins.

At step 1206, the dividing section 2060 appends identification information (ID) by class to each of the areas from C1 to C4.

Figure 15:
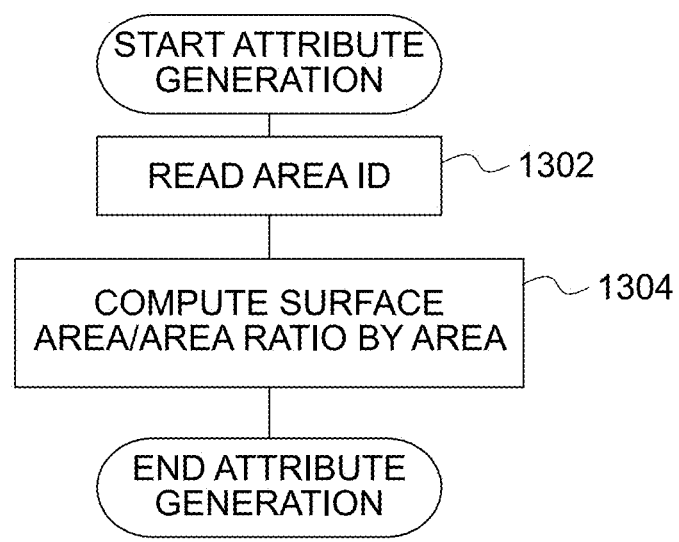
FIG. 15 is a flowchart of another example of attribute information generation processing of step 506 of FIG. 6.

When the identification information appending processing of step 1206 has finished, the area division processing of step 504 of FIG. 5 is ended, and the image processing transitions to the attribute information generation processing of step 506 (see FIG. 15).

At step 1302, the generating section 2062 reads the identification information (ID) for each of the plural areas.

At step 1304 the generating section 2062 computes attribute information for the areas divided by the watersheds (LH, LV). The attribute information for the areas of the choroidal vascular network divided by the watersheds is, for example, the following information.

Firstly: a total surface area of the plural choroidal blood vessels connected to the vortex vein (the surface area in the choroidal vascular image indicated by pixels of choroidal blood vessels connected to the vortex vein bulging portion).

The total surface area of the choroidal blood vessels is an area of the plural choroidal blood vessels that are themselves connected to the same vortex vein. In the example of FIG. 20, there are areas from an area A1 of the plural choroidal blood vessels connected to the first vortex vein VV1 to an area A4 of the plural choroidal blood vessels themselves that are connected to the fourth vortex vein VV4. For example, in the first vortex vein VV1 this corresponds to the surface area of the pixels of the white area A1 indicating the choroidal blood vessels. The surface area of each of the areas is computed based on the number of pixels and the pixel positions in the respective surface areas SA1 to SA4 of the areas A1 to A4. The reason for considering the pixel positions is in order to take into consideration the point that the surface area per single pixel differs between at the periphery of the image and at the center of the image because the choroidal blood vessels lie on a spherical surface.

Secondly: a surface area and shape of a convex hull area for an area in which there are plural choroidal blood vessels connected to a vortex vein present in the area (when the choroidal blood vessels are considered as rivers then the convex hull area corresponds to a drainage basin surface area of the rivers).

The convex hull (or convex envelope) area is a minimum convex set to include the plural choroidal blood vessels connected to the same vortex vein. In the example illustrated in FIG. 20, these are areas from a convex hull area B1 of the plural choroidal blood vessels connected to the first vortex vein VV1 to a convex hull area B4 of the plural choroidal blood vessels connected to the fourth vortex vein VV4. For example, in the convex hull B4 of the fourth vortex vein VV4 example, this indicates a fan shaped area in which leading ends of the choroidal blood vessels are tied in a fan shape focusing on the vortex vein bulging portion of the fourth vortex vein VV4.

The surface areas SB1 to SB4 of the respective areas B1 to B4 are then computed. A value is, for example, computed to indicate how close the shape of each of the areas B1 to B4 is to a circle. More specifically, the circularity is computed. The generating section 2062 computes a center of a hypothetical circle for each of the areas B1 to B4, calculates a specific spacing of a distance between a position of an area line demarcating the area and the center of the hypothetical circle, and calculates the circularity by taking a difference between the maximum value and the minimum value of this distance.

Thirdly: a surface area of each of plural (for example, four) areas C1 to C4 obtained by dividing the choroidal vascular image using the first watershed LH and the second watershed LV as the boundaries. Moreover, not only the surface area, but morphological feature information, such as information indicating an area ratio and shape (polygon information and the like) may be employed therefor.

In cases in which the area ratio is employed, the ratio of the surface area of each of the areas to the surface area of other areas partly overlapping with the respective areas may be employed.

In the example illustrated in FIG. 20, the respective surface areas of areas A1 to A4 of the plural choroidal blood vessels themselves that are connected to the same vortex vein are denoted SA1 to SA4. The respective surface areas of convex hull areas B1 to B4 of areas in which plural choroidal blood vessels connected to one vortex vein are present are denoted SB1 to SB4. The respective surface areas of plural (for example four) areas C1 to C4 obtained by dividing the choroidal vascular image using the first watershed LH and the second watershed LV as boundaries are denoted SC1 to SC4.

Area ratios are, more specifically, for the area A1, a ratio of between the surface area of area A1 and the surface area of area B1 (for example, SB1/SA1), and a ratio of between the surface area of area A1 and the surface area of area C1 (for example, SC1/SA1). Similarly, there are, for example, SB2/SA2, SC3/SA3 for areas A2, A3, and, for example, SA1/SB1 to SB4/SC4 for areas B1 to C4. Note that the denominator and the numerator may be swapped around.

When the attribute information computation processing of step 1304 has finished, the attribute information generation processing of step 506 of FIG. 5 is ended, and the image processing transitions to attribute appending processing of step 508.

At step 508 the processing section 208 appends an attribute to each of the areas. More specifically, the processing section 208 corresponds attribute information, for example surface areas and area ratios with the identification information (ID) for each of the areas and stores these in the storage device 254.

When the attribute appending processing of step 508 as described above is ended, the image processing transitions to step 510. At step 510 the color-coded painting section 2064 creates visibility data to make the areas visible according to the attributes of the areas in the following manner.

Mutually different colors are associated with the areas C1 to C4 derived with respect to the watersheds. For example, yellow is associated with area C1, orange with area C2, green with area C3, and blue with area C4. The color-coded painting section 2064 then identifies the corresponding color information associated with the respective area identification information C1 to C4. In such cases the attribute information is not computed.

Moreover, explanation follows regarding a method for creating the visibility data in cases in which the surface areas and the area ratios are computed. Note that the method for creating the visibility data in cases in which the area ratios are computed is similar to the method for creating the visibility data in cases in which the surface area is computed, and so explanation thereof will be omitted.

As described above, the surface area for each of the areas is surface areas SA1 to SA4 for the areas A1 to A4, surface areas SB1 to SB4 for the areas B1 to B4, and surface areas SC1 to SC4 for the areas C1 to C4.

The range of possible surface areas for the respective areas A1 to A4, B1 to B4, and C1 to C4 is divided into plural surface area ranges. For example, the possible range is divided into four surface area ranges. A mutually different color, for example yellow, orange, green, or blue is then associated with each surface area range.

At step 510 the color-coded painting section 2064 reads the surface area from the storage device 254 for each area class. The color-coded painting section 2064 determines which surface area range the read surface area falls in, and identifies the color associated with the surface area range it is determined to fall in.

When the visibility data creation processing of step 510 has finished, the image processing transitions to step 512. At step 512 the processing section 208 saves the visibility data in the storage device 254 associated with the identification information for each area.

Figure 21:
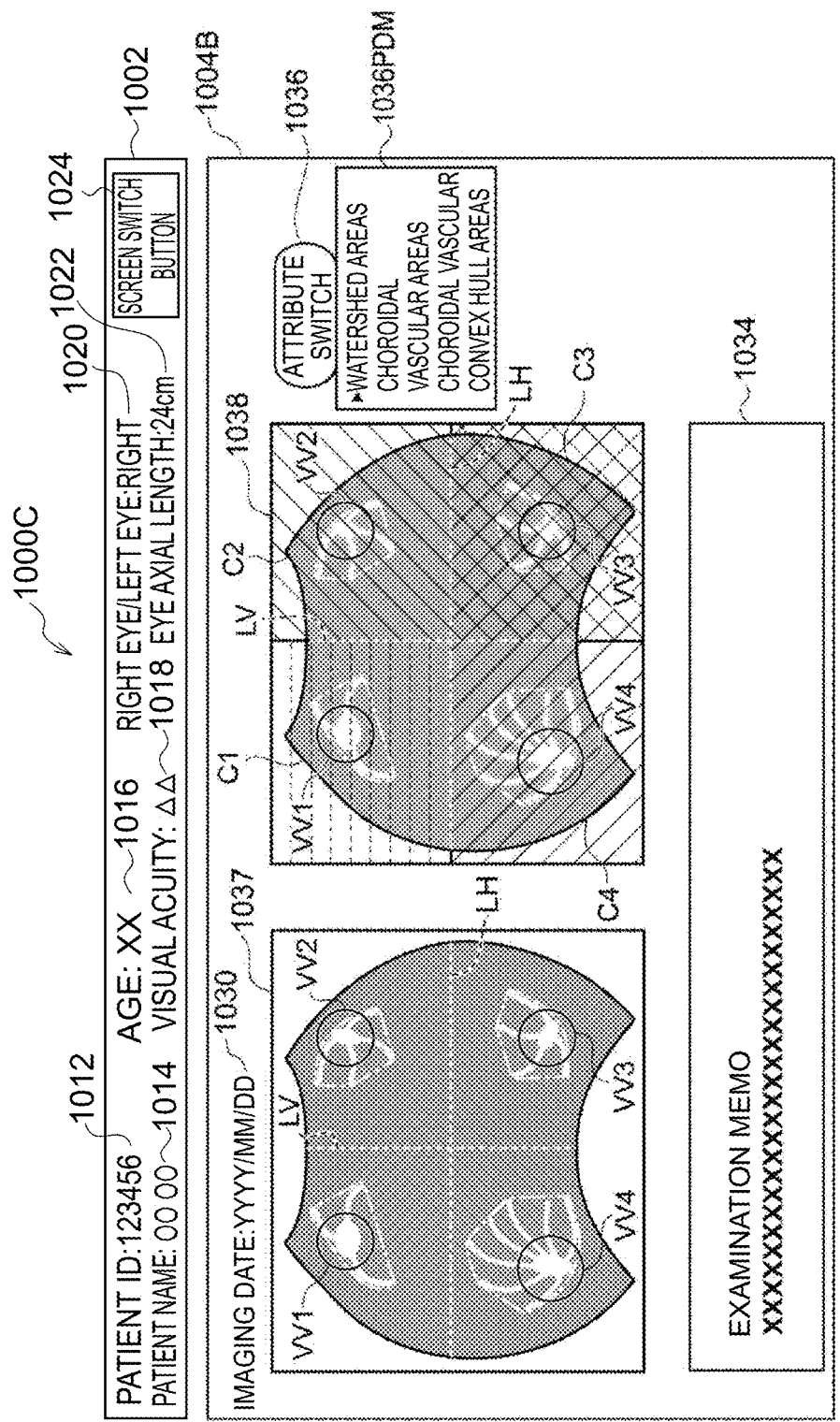
FIG. 21 is a diagram illustrating a third fundus image display screen 1000C.

Next, explanation follows regarding a third fundus image display screen 1000C displayed on a display by the viewer 150 of the second exemplary embodiment, with reference to FIG. 21.

The content of the third fundus image display screen 1000C is substantially similar to that of second fundus image display screen 1000B, and so the same reference numerals are appended to same parts, explanation thereof will be omitted, and explanation will focus on differing parts alone.

The third fundus image display screen 1000C includes an area overlay choroidal vascular image display field 1037 and a color coded area overlay choroidal vascular image display field 1038 instead of the UWF fundus image display field 1032A2, the area overlay UWF fundus image display field 1032B, and the brightness range color display field 1032C.

An image is displayed in the area overlay choroidal vascular image display field 1037 of each area of each class overlaid on the choroidal vascular image.

An image is displayed in the color coded area overlay choroidal vascular image display field 1038 of areas of stipulated classes overlaid on the choroidal vascular image in a color coded state.

The pull down menu 1036PDM includes "watershed areas", "choroidal vascular areas", and "choroidal vascular convex hull areas".

"Watershed areas" is an instruction to display an image in which watershed areas have been overlain on the choroidal vascular image in a color coded state.

"Choroidal vascular areas" is an instruction to display an image in which choroidal vascular areas have been overlain on the choroidal vascular image in a color coded state.

"Choroidal vascular convex hull areas" is an instruction to display an image in which choroidal vascular convex hull areas have been overlain on the choroidal vascular image in a color coded state.

In FIG. 21, when the "choroidal vascular convex hull areas" is selected, an image is displayed on the color coded area overlay choroidal vascular image display field 1038 in which the watershed areas are overlaid on the choroidal vascular image in a color coded state.

As explained above, in the second exemplary embodiment the fundus region of an ultra-wide field fundus image is divided into plural areas with respect to the watersheds, and attribute information is generated for each of the areas. Color information is generated to indicate the color for display corresponding to the respective attribute information for each of the areas. Each of the areas is displayed in the indicated color. This accordingly enables a discrimination to be ascertained between states of each area in the fundus and states of other areas.

In the first exemplary embodiment and the second exemplary embodiment described above, a UWF-SLO fundus image (UWF fundus image) obtained by imaging at an imaging angle of an internal illumination angle of 160° or greater is employed, however the technology disclosed herein is not limited thereto. A fundus image obtained by imaging at an imaging angle of an internal illumination angle of less than 160° but more than ( ) is applicable in the technology disclosed herein.

In the first exemplary embodiment and the second exemplary embodiment described above, each of the areas is displayed in a color associated with an attribute of the area, however the technology disclosed herein is not limited thereto. Display of each area with a density, flashing interval, or the like corresponding to the attribute of the area is also applicable in the technology disclosed herein.

In each of the examples described above, the image processing of FIG. 5 is executed by the server 140, however the technology disclosed herein is not limited thereto. For example, this processing may be executed by the ophthalmic device 110 or the viewer 150, or a separate other image processing device may be connected to the network 130 and the processing executed by this image processing device.

Although explanation has been given in the exemplary embodiments described above regarding an example in which a computer is employed to implement image processing using a software configuration, the technology disclosed herein is not limited thereto. For example, instead of the image processing being executed by a software configuration employing a computer, the image processing may be executed solely by a hardware configuration such as a field programmable gate array (FPGA) or an application specific integrated circuit (ASIC). Alternatively, a configuration may be adopted in which some processing out of the image processing is executed by a software configuration, and the remaining processing is executed by a hardware configuration.

Such technology disclosed herein encompasses cases in which the image processing is implemented by a software configuration utilizing a computer, and also image processing implemented by a configuration that is not a software configuration utilizing a computer, and encompasses the following first technology to third technology.

First Technology

An image processing device including: a dividing section that divides a fundus region of an ultra-wide field fundus image into plural areas including at least a first area and a second area; a first generating section that generates first attribute information indicating an attribute of the first area and second attribute information indicating an attribute of the second area; and a second generating section that generates first mode instruction information to instruct display of the first area in a first mode corresponding to the first attribute information and second mode instruction information to instruct display of the second area in a second mode corresponding to the second attribute information.

Note that the dividing section 2060 of the exemplary embodiment described above is an example of the "dividing section" of the above first technology, and the generating section 2062 is an example of the "first generating section" and the "second generating section" of the above first technology.

Second Technology

An image processing method including: a dividing section dividing a fundus region of an ultra-wide field fundus image into plural areas including at least a first area and a second area; a first generating section generating first attribute information indicating an attribute of the first area and second attribute information indicating an attribute of the second area; and a second generating section generating first mode instruction information to instruct display of the first area in a first mode corresponding to the first attribute information and second mode instruction information to instruct display of the second area in a second mode corresponding to the second attribute information.

The following third technology is proposed from the content disclosed above.

Third Technology

A computer program product for image processing, the computer program product including a computer-readable storage medium that is not itself a transitory signal, with a program stored on the computer-readable storage medium. The program causes a computer to execute processing including: dividing a fundus region of an ultra-wide field fundus image into plural areas including at least a first area and a second area: generating first attribute information indicating an attribute of the first area, and second attribute information indicating an attribute of the second area; and generating first mode instruction information to instruct display of the first area in a first mode corresponding to the first attribute information, and second mode instruction information to instruct display of the second area in a second mode corresponding to the second attribute information.

It must be understood that the image processing described above is merely an example thereof. Obviously redundant steps may be omitted, new steps may be added, and the processing sequence may be swapped around within a range not departing from the spirit of technology disclosed herein.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. An image processing method comprising:
   dividing, by one or more processors, a fundus region of an ultra-wide field fundus image of a fundus into a plurality of areas as a boundary with a blood vessel of the fundus;
   generating, by the one or more processors, primary information indicating whether each of the plurality of areas includes a partial area that is no blood flow or hardly any blood flow; and
   generating, by the one or more processors, based on the primary information, first mode instruction information to instruct a display to display an area including the partial area among the plurality of areas in a first mode, and second mode instruction information to instruct the display to display an area not including the partial area among the plurality of areas in a second mode.

2. The image processing method of claim 1, wherein the first mode instruction information is information on a first color and the second mode instruction information is information on a second color different from the first color.

3. The image processing method of claim 1, further comprising:
displaying, by the one or more processors, each of the plurality of areas in the first mode or the second mode, based on the first mode instruction information and the second mode instruction information.

4. The image processing method of claim 1, further comprising:
categorizing, by the one or more processors, areas including the partial area into the first mode and a mode different from the first mode, based on a plurality of attributes that are different to each other and are defined according to a condition of the partial area; and
displaying, by the one or more processors, the areas including the partial area in a mode corresponding to each of the categorized areas.

5. The image processing method of claim 4, wherein displaying the areas including the partial area in a mode corresponding to each of the categorized areas comprises:
displaying the areas including the partial area in different colors corresponding to each of the plurality of attributes.

6. The image processing method of claim 1, wherein dividing the fundus region into the plurality of areas comprises:
setting a boundary between the fundus region and a background region surrounding the fundus region, as an outline line in the area.

7. The image processing method of claim 1, wherein generating the primary information indicating whether each of the plurality of areas includes the partial area comprises:
detecting, as the partial area, an area having contiguous pixels equal to or darker than a predetermined darkness in the ultra-wide field fundus image.

8. The image processing method of claim 1, wherein generating the primary information indicating whether each of the plurality of areas includes the partial area comprises:
detecting whether the partial area is a non perfusion area.

9. The image processing method of claim 1, wherein generating the primary information indicating whether each of the plurality of areas includes the partial area comprises:
detecting whether the partial area is an avascular area.

10. An image processing device comprising:
a memory; and
one or more processors coupled to the memory,
wherein the one or more processors are configured to:
divide a fundus region of an ultra-wide field fundus image of a fundus into a plurality of areas as a boundary with a blood vessel of the fundus;
generate primary information indicating whether each of the plurality of areas includes a partial area that is no blood flow or hardly any blood flow; and
generate, based on the primary information, first mode instruction information to instruct a display to display an area including the partial area among the plurality of areas in a first mode, and generates second mode instruction information to instruct the display to display an area not including the partial area among the plurality of areas in a second mode.

11. The image processing device of claim 10, wherein the one or more processors are further configured to:
categorize areas including the partial area into the first mode and a mode different from the first mode, based on a plurality of attributes that are different to each other and are defined according to a condition of the partial area,
display the areas including the partial area in a mode corresponding to each of the categorized areas.

12. A non-transitory storage medium storing a program executable by a computer to perform image processing comprising:
dividing a fundus region of an ultra-wide field fundus image of a fundus into a plurality of areas as a boundary with a blood vessel of the fundus;
generating primary information indicating whether each of the plurality of areas includes a partial area that is no blood flow or hardly any blood flow; and
generating, based on the primary information, first mode instruction information to instruct a display to display an area including the partial area among the plurality of areas in a first mode, and second mode instruction information to instruct the display to display an area not including the partial area among the plurality of areas in a second mode.

13. The non-transitory storage medium of claim 12, wherein the image processing further comprises:
categorizing areas including the partial area to the first mode and a mode different from the first mode, based on a plurality of attributes that are different to each other and are defined according to a condition of the partial area; and
displaying the areas including the partial area in a mode corresponding to each of the categorized areas.

* * * * *